Aug. 30, 1955 R. S. LEMCKE ET AL Plant Pat. 1,414
APPLE TREE
Filed Oct. 12, 1954
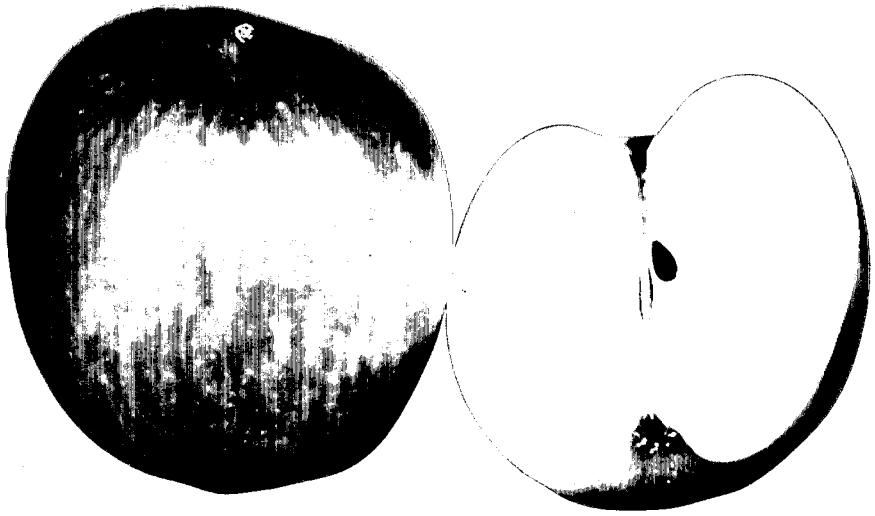
INVENTORS
Robert S. Lemcke &
Jacob A. Snyder
By Orville M. Kile
Plant Patent Agent United States Patent Office Plant Pat. 1,414
Patented Aug. 30, 1955

1,414

APPLE TREE

Robert S. Lemcke, Tieton, and Jacob A. Snyder, Wenatchee, Wash., assignors to Columbia & Okanogan Nursery Company, Wenatchee, Wash.

Application October 12, 1954, Serial No. 461,943

1 Claim. (Cl. 47—62)

The present invention relates to a new and useful variety of apple tree which was discovered at Tieton, Washington, in an orchard of Rome Beauty (unpatented) apple trees grown and owned by the first-named inventor. Its parentage is unknown but the new variety is apparently a whole-tree sport of a Rome Beauty tree.

The tree growth of our new variety is characteristic of that of Rome Beauty, but the fruit differs considerably in shape and coloring. The fruit is longer than that of Rome Beauty and has a deeper and more uniform basin. The color, which covers the entire surface, is brighter than that of Rome Beauty and develops at least two weeks earlier.

Asexual reproduction of this new variety was accomplished by means of budding and grafting by the second-named inventor, at a Wenatchee nursery of which he is part owner. Test plantings have been made at several locations and the distinguishing characteristics of the new variety appear to be permanent.

Accompanying illustrations are color photographs of a typical apple of this new variety and a cross-section of another specimen of the new variety. The appearance of the whole apple is as nearly correct as it is possible to show it. However, the cross-section shows a great deal more red than is typical in the fruit (due to imperfections of color photography). In fact, most of the fruits show no red at all in the flesh but are white, tinged with green or yellow.

In the following detailed description of the tree and fruit of this new variety, color plate references indicate Ridgway's Color Standards and Nomenclature. Other color nomenclature refers to the ordinary dictionary means of the term.

THE TREE

Growth: Moderately vigorous and medium sized.

Form: At first narrowly upright but later roundish and somewhat spreading and drooping.

Branches:

- *Lateral branches.*—Rather slender.
- *Bark.*—Mottled brownish-red and green; rather bright.
- *Lenticles.*—Moderate number; medium in size, scattering; conspicuous; round to oblong; raised.
- *Buds.*—Deeply set in bark; very short; broad; obtuse; appressed.
- *Twigs.*—Moderately stout and nearly straight; sometimes slender; medium length with short internodes.

Foliage: Leaves—rather small; long oval; often much reflexed on curved midrib; slightly waved; color light green. Serrations—very sharp; small; regular and fairly distinct. Surface—moderately smooth and shiny.

THE FRUIT

Maturity: November.

Season: Develops full color at least two weeks earlier than Rome Beauty grown under the same conditions.

Size: Medium to large. Averages 3 to 3½ inches in diameter.

Form: Long and blocky. Fairly symmetrical and uniform but sometimes with sides unequal.

Cavity: Deep and with considerable uniformity; obtuse and smooth; red.

Basin: Moderately deep to deep and uniform, narrow; sometimes abrupt; usually somewhat furrowed or wrinkled.

Stem: Long and slender. Clings to twig exceptionally well.

Skin:

- *Color and color distribution.*—On typical specimens full color of Scarlet (Pl. I) or slightly darker covers the entire surface, with underlying double striping of Carmine (Pl. I). One side of fruit is slightly darker than other but both sides are very bright. Surface is irregularly dotted with many minute dots of light yellow.
- *Texture.*—Thick, tough and able to stand handling remarkably well.

Flesh:

- *Texture.*—Firm; moderately fine-grained. Becomes mellow when stored.
- *Color.*—Typical fruit nearly white, with slight tinges of yellow or green. In some specimens there are tracings of red outlining the bundle area.
- *Flavor.*—Agreeably mild sub-acid.
- *Crispness and juiciness.*—Moderately crisp and very juicy at first, but later losing much of its juiciness.
- *Aroma.*—Slightly aromatic.
- *Quality.*—Very good.

Core:

- *Size.*—Core itself is small
- *Shape.*—Cone-shaped.
- *Bundle area.*—Large; symmetrical; halves nearly equal; sometimes outlined with red.
- *Lines.*—Distinct; yellow or red.
- *Carpels.*—Roundish to ovate, narrowing toward apex and base.

Seeds:

- *Number.*—8 to 12.
- *Size.*—Small to medium.
- *Color.*—Dark Brown.
- *Form.*—Slender, acute with rounded base.

Keeping quality: Excellent keeper, being held in cold storage until summer.

Having thus disclosed our invention, we claim:

The new and distinct variety of apple tree of the Rome Beauty type, substantially as herein disclosed, characterized particularly by its fruit having exceptionally good keeping qualities; long blocky shape with relatively deep and uniform basin; and early-developing, distinctive bright red coloring which covers the entire fruit.

No references cited.